(12) United States Patent
Phillips et al.

US010660945B2

(10) Patent No.: US 10,660,945 B2
(45) Date of Patent: May 26, 2020

(54) FLOWABLE HEMOSTATIC GEL COMPOSITION AND ITS METHODS OF USE (71) Applicant: Victor Matthew Phillips, Jefferson City, MO (US)

(72) Inventors: Victor Matthew Phillips, Jefferson City, MO (US); John Garner, West Lafayette, IN (US)

(73) Assignee: Victor Matthew Phillips, Jefferson City, MO (US)

( * ) Notice: Subject to any disclaimer, the term of this patent is extended or adjusted under 35 U.S.C. 154(b) by 439 days.

(21) Appl. No.: 15/195,087

(22) Filed: Jun. 28, 2016

(65) Prior Publication Data
US 2017/0035861 A1 Feb. 9, 2017

Related U.S. Application Data (63) Continuation-in-part of application No. 14/820,936, filed on Aug. 7, 2015.

(51) Int. Cl.
*A61K 38/48* (2006.01)
*A61K 38/36* (2006.01)
*A61L 24/10* (2006.01)
*A61L 24/08* (2006.01)

(52) U.S. Cl.
CPC ........ *A61K 38/4833* (2013.01); *A61K 38/363* (2013.01); *A61L 24/08* (2013.01); *A61L 24/106* (2013.01); *A61L 24/108* (2013.01); *C12Y 304/21005* (2013.01); *A61L 2400/04* (2013.01); *A61L 2400/06* (2013.01)

(58) Field of Classification Search
None
See application file for complete search history.

(56) References Cited

U.S. PATENT DOCUMENTS

| 5,510,102 | A | 4/1996 | Cochrum |
| 5,578,661 | A * | 11/1996 | Fox ...................... A61L 15/225 |
| | | | 514/944 |
| 6,162,241 | A | 12/2000 | Coury et al. |
| 6,706,690 | B2 | 3/2004 | Reich et al. |
| 8,512,729 | B2 | 8/2013 | Wallace et al. |
| 8,603,511 | B2 | 12/2013 | Wallace et al. |
| 8,642,831 | B2 | 2/2014 | Larsen et al. |
| 8,703,170 | B2 | 4/2014 | Hedrich et al. |
| 8,940,335 | B2 | 1/2015 | Goessl |
| 8,999,376 | B2 | 4/2015 | Ericson |
| 9,017,664 | B2 | 4/2015 | Preiss-Bloom et al. |
| 9,662,400 | B2 | 5/2017 | Smith et al. |
| 2002/0042378 | A1 | 4/2002 | Reich et al. |
| 2002/0131933 | A1 | 9/2002 | Delmotte |
| 2002/0193448 | A1 | 12/2002 | Wallace et al. |
| 2004/0136977 | A1 | 7/2004 | Miyamoto et al. |
| 2004/0214770 | A1 | 10/2004 | Reich et al. |
| 2005/0004158 | A1 | 1/2005 | Iyer et al. |
| 2005/0058688 | A1 | 3/2005 | Boerger et al. |
| 2005/0281873 | A1 | 12/2005 | Badwan et al. |
| 2006/0018973 | A1 | 1/2006 | Kim et al. |
| 2007/0071728 | A1 | 3/2007 | Ko et al. |
| 2007/0148161 | A1 | 6/2007 | Delmotte |
| 2008/0187591 | A1 | 8/2008 | Rhee et al. |
| 2009/0155342 | A1 | 6/2009 | Diegelmann et al. |
| 2010/0292624 | A1 | 11/2010 | Diegelmann et al. |
| 2010/0316739 | A1 | 12/2010 | Nisis |
| 2012/0207813 | A1 | 8/2012 | Rhee et al. |
| 2013/0129710 | A1 | 5/2013 | Nordhaus et al. |
| 2013/0224712 | A1 | 8/2013 | Day et al. |
| 2013/0287817 | A1 | 10/2013 | Drapeau et al. |
| 2013/0287837 | A1 | 10/2013 | MacPhee et al. |
| 2014/0072614 | A1 | 3/2014 | Rhee et al. |
| 2014/0187492 | A1 | 7/2014 | Falus et al. |
| 2014/0287061 | A1 | 9/2014 | Landolina |
| 2014/0314706 | A1 | 10/2014 | Diehn et al. |
| 2014/0369991 | A1 | 12/2014 | Schutte et al. |
| 2014/0378928 | A1 | 12/2014 | Hedrich et al. |
| 2015/0037774 | A1 | 2/2015 | Day et al. |

FOREIGN PATENT DOCUMENTS

| EP | 2455109 | A2 | 5/2012 |
| JP | 2000290633 | A | 10/2000 |
| WO | 9617633 | A1 | 6/1996 |
| WO | 9640174 | A1 | 12/1996 |
| WO | 9808550 | A1 | 3/1998 |
| WO | 9907417 | A1 | 2/1999 |
| WO | 0076533 | A1 | 12/2000 |
| WO | 02096978 | A1 | 12/2002 |

(Continued)

OTHER PUBLICATIONS

Kang, Pei-Leun, et al. "Development and assessment of hemostasis chitosan dressings." Carbohydrate polymers 85.3 (2011): 565-570. (Year: 2011).*
International Search Report and Written Opinion of International Application No. PCT/US2016/045126, dated Oct. 10, 2016, 10 pages.
Zhao, Yet al. Pluronic-poly (acrylic acid)-cysteine/Pluronic L121 mixed micelles improve the oral bioavailability of paclitaxel. Drug development and industrial pharmacy. Nov. 1, 2014. vol. 40. No. 11; pp. 1483-1493.
Sionkowska, A et al. Molecular interactions in collagen and chitosan blends. Biomaterials. Feb. 29, 2004. vol. 25. No. 5; pp. 795-801.
Gaffney, PJ et al. The International and "NIH" units forthrombin—how do they compare? Thrombosis and Flaemostasis. Sep. 1995 vol. 74. No. 3; abstract.

(Continued)

*Primary Examiner* — Robert J Yamasaki
(74) *Attorney, Agent, or Firm* — Armstrong Teasdale LLP (57) ABSTRACT

A flowable hemostatic gel composition is provided for use at a site of a defect within a biological tissue. The flowable hemostatic gel composition includes a flowable gel solution that includes a biopolymer dissolved in a first solvent. The biopolymer is configured to cross-link with red blood cells at the site to facilitate clot formation at the site. The flowable hemostatic gel composition also includes at least one additional active agent.

17 Claims, 5 Drawing Sheets

(56) References Cited

FOREIGN PATENT DOCUMENTS

| WO | 03035115 A2 | 5/2003 |
| --- | --- | --- |
| WO | 2004028578 A1 | 4/2004 |
| WO | 2004032713 A2 | 4/2004 |
| WO | 2004112864 A2 | 12/2004 |
| WO | 2006057011 A2 | 6/2006 |
| WO | 2006088912 A2 | 8/2006 |
| WO | 2007013717 A1 | 2/2007 |
| WO | 2008016983 A2 | 2/2008 |
| WO | 2008076407 A2 | 6/2008 |
| WO | 2010057177 A2 | 5/2010 |
| WO | 2010107794 A2 | 9/2010 |
| WO | 2010134988 A1 | 11/2010 |
| WO | 2011003155 A1 | 1/2011 |
| WO | 2011084326 A2 | 7/2011 |
| WO | 2011124640 A1 | 10/2011 |
| WO | 2011151384 A1 | 12/2011 |
| WO | 2011151386 A1 | 12/2011 |
| WO | 2011151400 A1 | 12/2011 |
| WO | 2012030805 A2 | 3/2012 |
| WO | 2012122044 A2 | 9/2012 |
| WO | 2013003045 A2 | 1/2013 |
| WO | 2013060769 A2 | 5/2013 |
| WO | 2013096605 A1 | 6/2013 |
| WO | 2013116633 A2 | 8/2013 |
| WO | 2013126707 A1 | 8/2013 |
| WO | 2013185776 A1 | 12/2013 |
| WO | 2014142915 A1 | 9/2014 |
| WO | 2014160136 A1 | 10/2014 |

OTHER PUBLICATIONS

International Search Report and Written Opinion, dated Sep. 7, 2017, for co-pending International patent application No. PCT/US2017/038113.

Calvo, Pilar, et al. "Novel hydrophilic chitosan-polyethylene oxide nanoparticles as protein carriers." Journal of Applied Polymer Science 63.1(1997):125-132. (Year 1997).

Piai, Juliana F., et al. "Kinetic study of Chondroitin Sulphate release from Chondroitin Sulphate/Chitosan complex hydrogel." Journal of Molecular Liquids 156.1 (2010): 28-32. (Year: 2010).

* cited by examiner

FLOWABLE HEMOSTATIC GEL COMPOSITION AND ITS METHODS OF USE

CROSS REFERENCE TO RELATED APPLICATIONS

This application is a continuation-in-part of U.S. patent application Ser. No. 14/820,936, filed Aug. 7, 2015, which is incorporated herein by reference in its entirety.

BACKGROUND

The subject matter described herein relates generally to hemostatic compositions and, more particularly, to flowable hemostatic gel compositions configured for introduction to a site of a surgical incision or other defect within a biological tissue.

It is necessary to inhibit bleeding from such sites, such as during and after a surgical procedure, to minimize risk to a subject. One known method to inhibit bleeding at such a site involves suturing. However, many defects within biological tissue, such as but not limited to those resulting from arteriotomies, involve internal incisions that are not easily accessible by suturing instruments. Other known methods to inhibit bleeding at such a site include an application of pressure manually and/or using a hemostatic device, and/or a use of absorbent materials, such as gauze and/or sponges. However, an effectiveness of such methods is limited for at least some defects within biological tissue after the procedure is complete. In addition, hemostatic gel compounds that include biopolymer materials such as chitosan and/or enzymatic clotting factors such as thrombin are known for treating skin wounds. However, an ability to deliver such known gel compounds to an internal site is limited.

BRIEF SUMMARY

In one aspect, a method of inhibiting bleeding from a site of a defect within a biological tissue is provided. The method includes applying a flowable hemostatic gel composition to the site such that a biopolymer of the flowable hemostatic gel composition cross-links with red blood cells at the site to facilitate clot formation at the site. The flowable hemostatic gel composition includes a flowable gel solution that includes the biopolymer dissolved in a first solvent, and at least one additional active agent.

In another aspect, a flowable hemostatic gel composition is provided for use at a site of a defect within a biological tissue. The flowable hemostatic gel composition includes a flowable gel solution that includes a biopolymer dissolved in a first solvent. The biopolymer is configured to cross-link with red blood cells at the site to facilitate clot formation at the site. The flowable hemostatic gel composition also includes at least one additional active agent.

DETAILED DESCRIPTION

The compositions and methods described herein relate to the inhibition of blood loss from a surgical incision or other defect within biological tissue of a subject and, more particularly, to a flowable hemostatic gel composition and methods of inhibiting blood flow from a subject using the flowable hemostatic gel composition. The flowable hemostatic gel composition includes a gel solution formed from a hemostatic biopolymer dissolved in a first solvent. The flowable hemostatic gel composition further includes at least one additional active agent. For example, the at least one additional active agent is provided by pre-dissolving it into the gel solution. In some embodiments, the at least one additional active agent includes a clotting agent, such as, but not limited to, thrombin. Additionally or alternatively, the at least one additional active agent includes a bioadhesive additive, such as, but not limited to, poly(acrylic acid). In some embodiments, the flowable hemostatic gel composition further includes a flowable hardener solution that interacts with the gel solution to facilitate an improved occlusion and/or strength of the gel after application. For example, the hardener solution includes sodium tripolyphosphate (NaTPP) dissolved in a second solvent.

For example, but not by way of limitation, the defect within biological tissue is associated with a medical procedure, such as, but not limited to, general surgery, thoracic/pulmonary surgery, colon resection, hepatobiliary surgery, pancreatic surgery, gynecologic surgery, orthopedic surgery, trauma surgery, ear-nose-throat (ENT) surgery, cosmetic surgery, urological procedures, neurosurgery, and cardiovascular surgery. In some embodiments, the defect is suture lines created in one of aortic root repair, aortic arch repair, aortotomy, aortic reconstruction, CABG, LVAD implantation, carotid endarterectomy, abdominal aortic aneurysm repair, and femoral bypass (fem-fem bypass or fem-pop bypass).

The flowable nature of the flowable hemostatic gel composition facilitates application of the biopolymer and the at least one additional active agent directly to all portions of the site of the surgical incision or other defect, and the surrounding biological tissues. After flowable introduction of the composition to the site, such as but not limited to by injection, the composition inhibits blood loss from the incision or other defect. For example, the biopolymer of the flowable hemostatic gel composition rapidly cross-links with red blood cells at the site to facilitate clot formation at the site. Moreover, the at least one incorporated active agent is released in active form to further facilitate inhibition of blood loss from the site by, for example, enhancing blood clotting and/or adhesion of the gel to the tissues surrounding the site. In certain embodiments, the at least one active agent is selected to provide an additional benefit, such as to prevent infection or otherwise accelerate healing. The flowable hemostatic gel composition safely biodegrades in vivo, eliminating a need for any secondary removal process.

In some embodiments, the flowable hemostatic gel composition includes a gel solution formed from the biopolymer dissolved in a first solvent. For example, the gel solution includes chitosan dissolved in a dilute acid selected from a lactic acid solution or an acetic acid solution. In alternative embodiments, the biopolymer and first solvent of the gel solution are selected to be any suitable materials, as described in detail below.

The gel solution is formulated to enable at least one property such as, but not limited to, viscosity or injectability of the gel solution; hemostatic properties of the gel solution; suitability of the flowable hemostatic gel composition for certain surgical methods and/or injection devices; and any other relevant property. The properties of the flowable hemostatic gel composition are governed by at least one of the composition of the gel solution; the selection of the at least one additional active agent in the flowable hemostatic gel composition; the method of introducing the flowable hemostatic gel composition to the incision site; and any other relevant property.

In certain embodiments, the biopolymer includes at least one polycationic polymer. Without being limited to any particular theory, the charges distributed within the polycationic polymer impart bioadhesive properties to enable the binding of a hemostatic gel containing the polycationic polymers to negatively charged surfaces including, but not limited to, biological tissues in the vicinity of a site of a biological defect. Thus, after flowable introduction to the site, the polycationic biopolymers cross-link with negatively charged red blood cells at the site to facilitate clot formation at the site, and further link the clot to the biological tissues proximate the site to facilitate clot retention at the site. Non-limiting examples of polycationic polymers suitable for inclusion in the gel solution include: chitosan, chitin, diethylaminoethyl-dextran, diethylaminoethyl-cellulose, diethylaminoethyl-agarose, diethylaminoethyl-alginate, any other polymer modified with a diethylaminoethyl group, any polymer containing a plurality of protonated amino groups, any polypeptide having an average residue isoelectric point above about 7, and any combination thereof.

In some embodiments, chitosan is selected as the polycationic polymer. Chitosan, as used herein, describes a naturally occurring linear polysaccharide composed of randomly distributed β-(1-4)-2-amino-2-D-glucosamine (deacetylated) and β-(1-4)-2-acetamido-2-D-glucoseamine (acetylated) units. Chitosan may be derived from chitin, a naturally occurring polymer isolated from fungi, mollusks, or from the exoskeletons of arthropods (e.g., crustaceans and insects). Chitosan is produced by subjecting chitin to a process of alkaline deacetylation. As described more generally above, without being limited to any particular theory, positive charges along the backbone of chitosan cause it to interact electrostatically with negatively charged blood cells, thus creating a sticky interface between the chitosan within the hemostatic hydrogel composition and red blood cells proximate the site. In addition, chitosan is also known to possess inherent anti-microbial properties.

In certain embodiments, the chitosan is produced using an alkaline deacetylation of chitin using a strong alkaline solution according to suitable methods. Typically, any chitin-based biopolymer with a degree of deacetylation greater than about 50% is referred to as chitosan. The degree of deacetylation of the chitosan may influence the characteristics of the hemostatic gel in which the chitosan is included. Non-limiting examples of characteristics of the hemostatic gel that may be influenced by the degree of acetylation of the chitosan include bioadhesive properties, and resistance to premature degradation in vivo at the surgical site.

The chitosan is provided in any suitable form including, but not limited to, powder, coarse ground flakes, or dissolved in a weak acid solvent. In some embodiments, the molecular weight of the chitosan is in a range from about 60 kDaltons to about 375 kDaltons (viscosity-average molecular weight $M_v$). Without being limited to any particular theory, the inclusion of chitosan of relatively higher molecular weight, such as at least 150 kDaltons, results in relatively slower degradation in vivo.

Chitosan is degraded in vivo by, for example, lysozyme, N-acetyl-o-glucosaminidase, and lipases, and the byproducts of chitosan degradation are saccharides and glucosamines that are gradually absorbed by the body. Therefore, no secondary process for removal from the body is required. Chitosan compositions having a 50% degree of deacetylation are highly degradable in vivo. As the degree of deacetylation increases, chitosan becomes increasingly resistant to degradation. Chitosan compositions having a degree of deacetylation that is higher than 95% degrade slowly over weeks or months. In certain embodiments, the degree of deacetylation of the chitosan in the gel solution is in a range from about 50% to about 100%. Moreover, in some embodiments, the degree of deacetylation is in a range from about 50% to about 80%. Moreover, in certain embodiments, the degree of deacetylation is in a range from about 65% to about 80%. In particular embodiments, the degree of deacetylation of the chitosan in the gel solution is about 75%.

In certain embodiments, the first solvent is selected to be a dilute acid solution, such as an aqueous solution that includes at least one of acetic, citric, oxalic, proprionic, ascorbic, hydrochloric, formic, lactic, or any other suitable organic or inorganic acid, in a range from about 0.1% to about 5% (v/v). For example, at least one polycationic polymer selected as the biopolymer is substantially insoluble in water and organic solvents, but is fairly soluble in dilute acid solutions. In some embodiments, the dilute acid is selected to influence at least one property of the gel solution including, but not limited to, susceptibility to degradation in vivo. Additionally or alternatively, a concentration of the dilute acid and/or a time period over which the chitosan is dissolved in the dilute acid is selected to influence at least one property of the gel solution, including, but not limited to, susceptibility to degradation in vivo. As one example, the dilute acid is 1% L-lactic acid (v/v). As another example, the dilute acid is 1% acetic acid (v/v).

In some embodiments, the concentration of the biopolymer dissolved in the first solvent is selected to enable delivery of an effective amount of the biopolymer while maintaining a flowable viscosity of the gel solution or flowable hemostatic gel composition. For example, the gel solution includes 1% w/v chitosan dissolved in 1% acetic acid, and has a viscosity in a range from about 200 centipoise (cP) to about 2000 cP. For another example, the gel solution includes 1% w/v chitosan of a relatively high molecular weight, as described above, dissolved in 1% acetic acid, and the gel solution has a viscosity in a range from about 800 cP to about 2000 cP. For another example, the gel solution includes within a range of 2-3% w/v chitosan of a relatively high molecular weight dissolved in 1% L-lactic acid, and the gel solution has a viscosity of about 1500 cP. In certain embodiments, a strength of the acid is selected to result in a pH of at least about 4. In particular embodiments, the strength of the acid is selected to result in a pH of at least about 2.

In some embodiments, the at least one additional active agent is selected to include at least one clotting agent. Without being limited to any particular theory, the at least one additional active agent is incorporated into the hemostatic gel composition such that it is released from the resulting clot in a predetermined release profile. Non-limiting examples of clotting agents suitable for inclusion in the hemostatic gel composition include thrombin, fibrinogen, and any combination thereof. As used herein, "U" refers to an NIH-defined activity unit that corresponds to about 0.324 µg of enzymatically active thrombin. For example, the gel solution includes an amount of thrombin in a range from about 0.5 U to about 200 U per gram of chitosan in the gel solution. For another example, the gel solution includes an amount of thrombin in a range from about 2 U to about 160 U per gram of chitosan in the gel solution. In certain embodiments, a given amount of thrombin combined with chitosan results in greater thrombin enzymatic activity than does the given amount of thrombin in an absence of chitosan.

In some embodiments, higher amounts of chitosan result in increased activity of the thrombin. In certain embodiments, an amount of thrombin included in the flowable hemostatic gel composition is selected by a physician depending on factors associated with the patient.

The at least one clotting agent is incorporated into the flowable hemostatic gel composition in any suitable fashion. For example, the at least one clotting agent is dissolved into the gel solution at any suitable time prior to injection at the site.

Certain clotting agents, such as, but not limited to, thrombin, include protein-based enzymes subject to denaturing or damage that reduce a capability to perform enzymatic activity. In certain embodiments, the gel solution is formulated to maintain the clotting agent in an enzymatically active state. For example, the ingredients of the gel solution may be selected to maintain parameters within suitable ranges to facilitate maintaining the clotting agent in an enzymatically active state. Non-limiting examples of solution conditions selected to maintain the clotting agent in an enzymatically active condition include pH, ionic concentrations, temperature, and any other relevant solution parameter.

As one example, the gel solution includes 2% w/v chitosan dissolved in a 1% (v/v) aqueous solution of L-lactic acid. Dissolving active thrombin in the gel solution and storing the thrombin-loaded gel solution at room temperature does not substantially reduce enzymatic activity of the thrombin. Moreover, maintaining the resulting flowable gel composition at 37 degrees C. for a period of time ranging from about 30 minutes to several hours does not substantially reduce the enzymatic activity of the thrombin.

A predetermined release profile of each clotting agent from the flowable hemostatic gel composition after flowable introduction to the site is any suitable release profile. In certain embodiments, the predetermined release profile is influenced by at least one factor such as, but not limited to, an amount of the clotting agent loaded in the flowable hemostatic gel composition, an incubation time of the clotting agent added to the gel solution, if any, with the biopolymer in the gel solution, and the manner and/or timing of mixing the gel solution. In some embodiments, the clotting agent is released at a relatively steady (zero-order) rate. In other embodiments, the release profile is characterized by an initial release of the clotting agent at a relatively high rate, followed by an extended release at a relatively lower steady rate.

For example, the clotting agent is thrombin, and the release profile is selected based on at least one factor such as, but not limited to, the type and size of a surgical incision creating the defect in the tissue, the method of application of the flowable hemostatic gel composition, and/or the amount of gel applied to the site. As another example, the gel solution includes 2% w/v chitosan dissolved in a 1% (v/v) aqueous solution of L-lactic acid, and thrombin is dissolved in the gel solution. The gel solution is incubated at room temperature for a period of time ranging from about 30 minutes to overnight prior to use in the hemostatic gel composition to enable the thrombin to form complexes with, or otherwise adhere to, the biopolymer in the gel solution, thereby forming a depot from which the thrombin may be released from the applied composition according to the predefined release profile.

In certain embodiments, the at least one additional active agent is selected to include at least one bioadhesive agent, and the flowable hemostatic gel composition further includes a flowable hardener solution that includes a cross-linking agent dissolved in a second solvent. Upon interaction with the cross-linking agent in the hardener solution, the biopolymers within the gel solution cross-link to form a bioadhesive layer adhered robustly over the defect and surrounding biological tissues. As described above, the defect may include a wound, an incision or other defect associated with a surgical procedure, or any other defect within one or more biological tissues of a subject.

In some embodiments, the flowable hemostatic gel composition is formed at least partially by mixing the gel solution, which contains the hemostatic biopolymer dissolved in the first solvent, with a bioadhesive solution that contains the at least one additional bioadhesive agent dissolved in a third solvent. Non-limiting examples of additional bioadhesive agents include a high molecular weight polymer selected from poly(acrylic acid), poly(vinylpyrrolidinone), and poly(acrylamide-co-acrylic acid). In one embodiment, the at least one additional bioadhesive agent is dissolved in water at a concentration ranging from about 10% (w/v) to about 40% (w/v). In other embodiments, the at least one additional bioadhesive agent is dissolved in water at a concentration ranging from about 10% (w/v) to about 20% (w/v), from about 15% (w/v) to about 25% (w/v), from about 20% (w/v) to about 30% (w/v), from about 25% (w/v) to about 35% (w/v), and from about 30% (w/v) to about 40% (w/v).

In alternative embodiments, the at least one bioadhesive agent is incorporated into the flowable hemostatic gel composition in any suitable fashion. For example, at least one bioadhesive agent is dissolved directly into one or both of the gel solution and the hardener solution prior to mixture of the gel solution and the hardener solution proximate the site.

In one embodiment, the flowable hemostatic gel composition includes 2% chitosan (w/v) dissolved in 1% L-lactic acid as the gel solution, mixed with 25% w/v poly(acrylic acid) dissolved in water as the bioadhesive solution. In various embodiments, the gel solution and the bioadhesive solution are mixed at a volume ratio (volume of gel solution: volume of bioadhesive solution) ranging from about 0.33 to about 3. In various other embodiments, the volume ratio ranges from about 0.33 to about 1.0, from about 0.5 to about 1.5, from about 1.0 to about 2.0, from about 1.5 to about 2.5, and from about 2.0 to about 3. For example, in one embodiment, the flowable hemostatic gel composition includes a mixture ratio of about 25% (v/v) of the bioadhesive solution (25% w/v poly(acrylic acid) dissolved in water) and about 75% (v/v) of the gel solution (2% (w/v) chitosan dissolved in 1% L-lactic acid).

The cross-linking agent of the flowable hardener solution is selected for its capability to cross-link the biopolymer of the gel solution. For example, the cross-linking agent links chains of the biopolymer together to form a three-dimensional matrix of interconnected, linear, polymeric chains. In some embodiments, the linking of the chains of the biopolymer causes the flowable hemostatic gel composition to rapidly cure into the solid bioadhesive layer over the defect within the biological tissue. In certain embodiments, the cross-linking agent is selected based upon at least one of the type of the polycationic polymer in the gel solution, the desired degree or extent of cross-linking, biocompatibility, and any other suitable factor. Non-limiting examples of suitable crosslinking agents include sodium tripolyphosphate (NaTPP), ethylene glycol diglycidyl ether, ethylene oxide, glutaraldehyde, epichlorohydrin, diisocyanate, calcium chloride, and genipin. For example, in certain embodiments, the cross-linking agent is selected to result in a cure time of less than about 10 seconds after the gel solution and flowable hardener solution are mixed together. For another example, in certain embodiments, the cross-linking agent is selected to result in a cure time of less than about one of 7, 6, 5, 4, 3, or 2 seconds.

For example, in certain embodiments, the biopolymer of the gel solution is chitosan, and the cross-linking agent of the hardener solution is NaTPP. In some such embodiments, the hardener solution includes NaTPP dissolved in water in a range from about 0.1% w/v to about 20% w/v. Moreover, in some such embodiments, the hardener solution includes NaTPP dissolved in water in a range from about 0.3% w/v to about 10% w/v. Moreover, in some such embodiments, the hardener solution includes NaTPP dissolved in water in a range from about 1% w/v to about 2% w/v. Moreover, in some such embodiments, the hardener solution includes NaTPP dissolved in water at about 2% w/v.

In various embodiments, the volume of the hardener solution ranges from about 50% to about 200% of the volume of the gel solution. In various other embodiments, the volume of the hardener solution ranges from about 50% to about 100%, from about 75% to about 125%, from about 100% to about 150%, from about 125% to about 175%, and from about 150% to about 200% of the volume of the gel solution. In one embodiment, the flowable hemostatic gel composition includes the hardener solution and gel solution at a volume ratio of about 1:1 to form the bioadhesive layer over the defect within the biological tissue. Alternatively, the hardener solution is not used, and the cross-linking of the biopolymer with red blood cells at the site and/or the action of the at least one clotting factor at the site facilitates sufficient clotting at the site.

Figure 5:
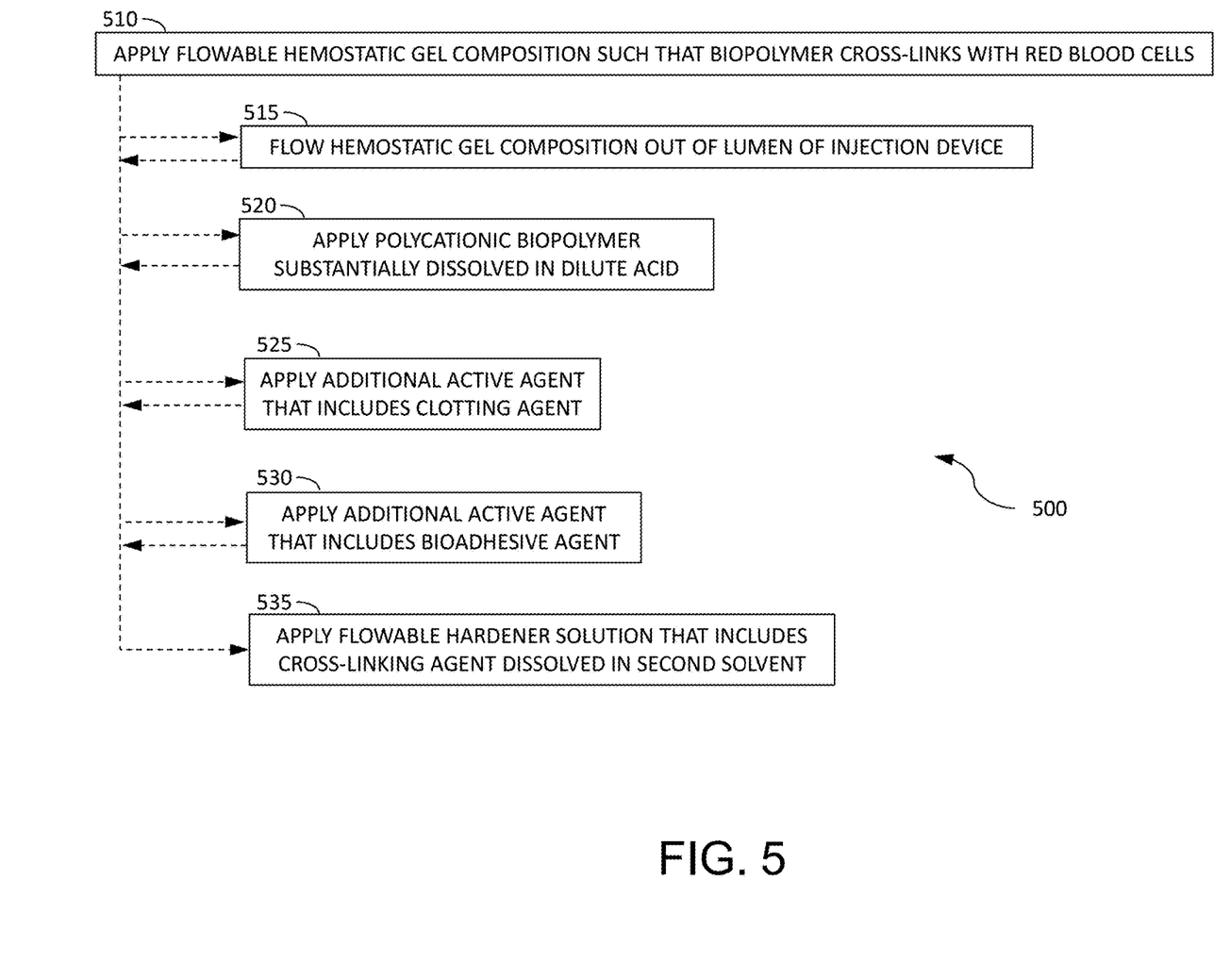
FIG. 5 is a flow diagram of an exemplary embodiment of a method of inhibiting bleeding from a site of a defect within a biological tissue.

FIG. 5 is a flow diagram of an exemplary embodiment of a method 500 of inhibiting bleeding from a site of a defect within a biological tissue. In the exemplary embodiment, method 500 includes applying 510 a flowable hemostatic gel composition to the site such that a biopolymer of the flowable hemostatic gel composition cross-links with red blood cells at the site to facilitate clot formation at the site. The flowable hemostatic gel composition includes a flowable gel solution that includes the biopolymer dissolved in a first solvent. The flowable hemostatic gel composition also includes at least one additional active agent.

In certain embodiments, the step of applying 510 the flowable hemostatic gel composition includes flowing 515 the flowable hemostatic gel composition out of a lumen of an injection device. For example, the site includes an internal incision, and an outlet of the lumen of the injection device is positioned adjacent the internal incision to enable the flowable hemostatic gel composition to flow directly onto the site. As described above, after the flowable hemostatic gel composition is applied, the biopolymer cross-links with red blood cells at the site to facilitate clot formation at the site, and/or links the clot to biological tissues proximate the site to facilitate clot retention at the surgical site. Thus, an ability to apply the hemostatic gel composition in flowable form facilitates achieving hemostasis even for, but not only for, incisions that are difficult to access using traditional methods.

In some embodiments, the step of applying 510 the flowable hemostatic gel composition includes applying 520 the biopolymer that is substantially polycationic dissolved in the first solvent that is a dilute acid. For example, but not by way of limitation, the biopolymer is substantially chitosan and the first solvent is lactic acid, as described above.

In certain embodiments, the step of applying 510 the flowable hemostatic gel composition includes applying 525 the at least one additional active agent that includes at least one clotting agent. For example, but not by way of limitation, the at least one clotting agent is at least one of thrombin and fibrinogen. In some embodiments, the biopolymer includes chitosan and the at least one clotting agent includes thrombin, such that a mass ratio of thrombin to chitosan (U:grams of chitosan) in the flowable hemostatic gel composition is in a range from about 0.5:1 to about 200:1, each U corresponding to about 0.324 µg of enzymatically active thrombin, as described above.

In some embodiments, the step of applying 510 the flowable hemostatic gel composition further includes applying 530 the at least one additional active agent that is at least one bioadhesive agent, and applying 535 a flowable hardener solution that includes a cross-linking agent dissolved in a second solvent. For example, but not by way of limitation, the at least one bioadhesive agent includes at least one of poly(acrylic acid), poly(vinylpyrrolidinone), and poly(acrylamide-co-acrylic acid), as described above. In some embodiments, the bioadhesive agent includes poly(acrylic acid) having a molecular weight of about 1800 Da. In one embodiment, the flowable hemostatic gel composition includes a mixture ratio of about 25% (v/v) of a bioadhesive solution and about 75% (v/v) of the gel solution, in which the bioadhesive solution is about 25% w/v poly(acrylic acid) dissolved in water, and the gel solution is about 2% (w/v) chitosan dissolved in 1% L-lactic acid, as described above.

Moreover, in certain embodiments, the flowable hardener solution includes sodium tripolyphosphate (NaTPP) dissolved in water. For example, but not by way of limitation, the flowable hardener solution includes about 2% w/v of sodium tripolyphosphate (NaTPP) dissolved in water, as described above. For example, in some embodiments, the flowable gel solution and the flowable hardener solution are applied at a volume ratio of about 1:1, as described above. In certain embodiments, the flowable gel solution and the flowable hardener solution are mixed together to form the flowable hemostatic gel composition immediately prior to and/or during their common introduction into a lumen of an injection device, and the flowable hemostatic gel composition is applied out of the lumen of the injection device directly to the site for rapid curing in situ. In other embodiments, the flowable gel solution and the flowable hardener solution are applied separately to the site, such as simultaneously or in sequence through a dual lumen injection device, and are allowed to mix at the site to form the flowable hemostatic gel composition for rapid curing in situ. Alternatively, the flowable gel solution and the flowable hardener solution are applied to the site in any suitable fashion. In certain embodiments, the method or sequence of introduction of the gel solution and the hardener solution to the surgical site influences one or more characteristics of the resulting hemostatic gel composition including, but not limited to, hardening time, gel strength, gel resistance to degradation, release rate of thrombin and/or other active agent included in the gel, and combinations thereof. Alternatively, the hardener solution is not used, and the cross-linking of the biopolymer with red blood cells and/or the action of the at least one clotting factor at the site facilitates sufficient clotting at the site.

EXAMPLES

The examples illustrate various embodiments of the disclosure.

Example 1: Mechanical Strength of Solid Hemostatic Gel Formed from the Flowable Hemostatic Gel Composition To evaluate the gel strength of various compositions of hemostatic gel as described herein above, the following experiments were conducted.

Chitosan (Aldrich Cat #419419, Sigma-Aldrich, St. Louis, Mo.) was dissolved at 2% w/v in a first solvent solution of 1% v/v L-lactic acid to form a gel solution. Sodium tripolyphosphate (NaTPP, Aldrich Cat #238503) was dissolved in a second solvent of de-ionized water ($DiH_2O$) to form a series of hardener solutions in the respective amounts of 0.3% w/v, 0.5% w/v, 0.7% w/v, 1% w/v, 2% w/v, and 10% w/v NaTPP.

To form the solid hydrogel samples, 0.5 ml of gel solution and 0.5 ml of hardener solution at the various concentrations (see Table 1) were added by pipette to a two-mL microfuge tube, such that a total volume of the flowable hemostatic gel composition was constant. Each sample was mixed and equilibrated overnight in a 100 RPM/37° C. shaking incubator.

Mechanical testing was performed on each resulting solid hydrogel sample using a TA.XTplus analyzer. A 0.25-inch steel ball was forced into the solid hydrogel at a crosshead speed of 1 mm/sec to a depth of 3.2 mm, in order to immerse the steel ball up to the ball's midpoint, and testing was initiated at 2 g of resistance force. The maximum resistance force encountered during the test was recorded to determine each sample's gel strength. Triplicate mechanical testing was performed for each NaTPP concentration.

Figure 1:
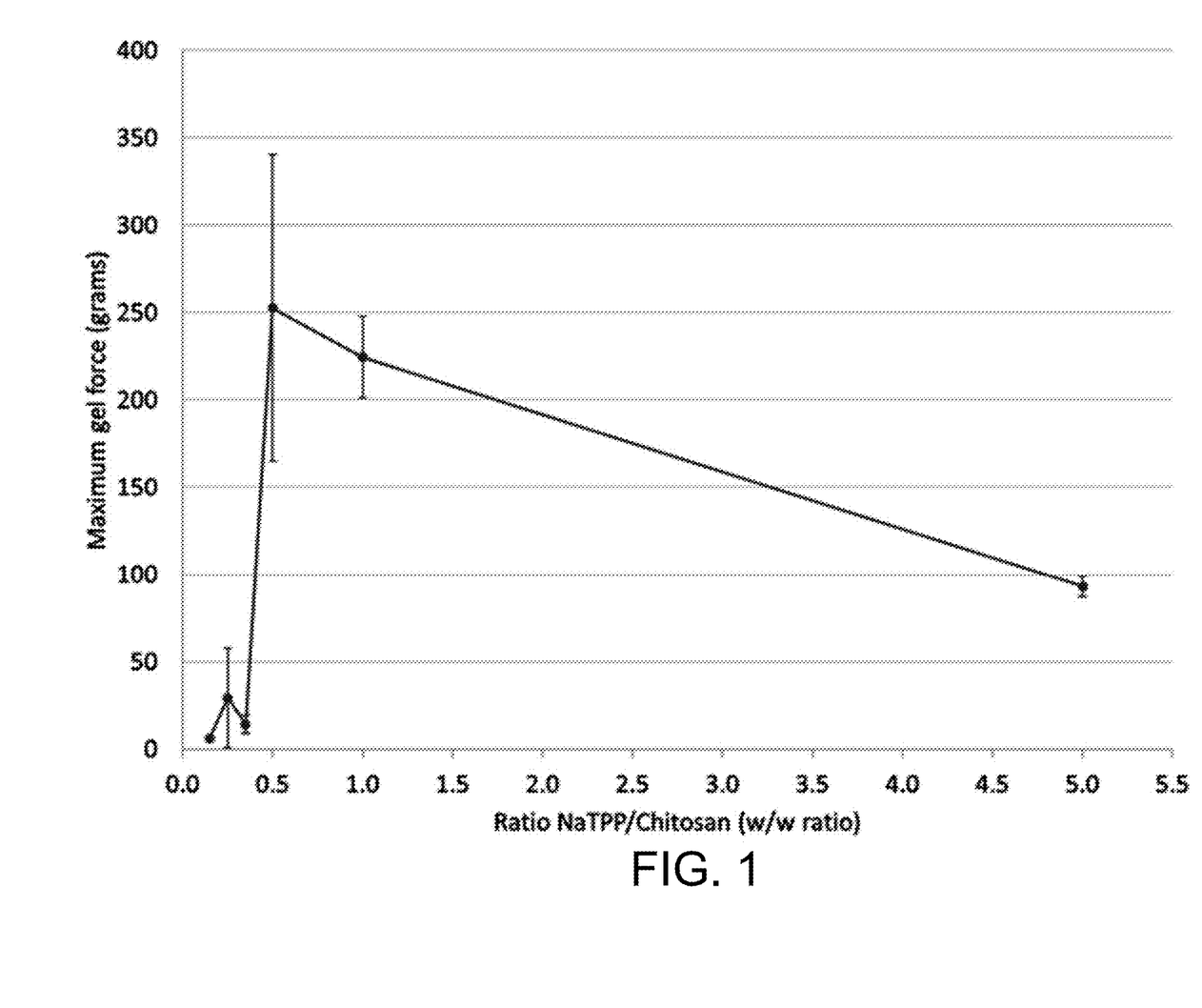
FIG. 1 is a graph summarizing a gel strength as a function of sodium tripolyphosphate:chitosan mass ratio for various hemostatic gel compositions.

Table 1 below summarizes the results of the mechanical testing. FIG. 1 is a graph summarizing the maximum gel force obtained for each sample as a function of the NaTPP:chitosan mass ratio. The gel strength was observed to increase as the NaTPP content of the gel samples increased, up to a maximum gel strength at a NaTPP:chitosan mass ratio of 0.5:1. NaTPP:chitosan mass ratios above 0.5 resulted in successively decreasing gel strengths, although the gel strengths remained substantial.

TABLE 1

Mechanical Strength of Hemostatic Gel Compositions.

| Gel Composition (all quantities in % w/v) | NaTPP/Chitosan mass ratio (w/w) | Max Force (g) mean ± SD (N = 3) |
|---|---|---|
| 0.5 ml of 2% CGF plus 0.5 ml 0.3% NaTPP | 0.2 | 6.0 ± 1.3 |
| 0.5 ml of 2% CGF plus 0.5 ml 0.5% NaTPP | 0.3 | 29.3 ± 28.4 |
| 0.5 ml of 2% CGF plus 0.5 ml 0.7% NaTPP | 0.4 | 14.1 ± 5.0 |
| 0.5 ml of 2% CGF plus 0.5 ml 1% NaTPP | 0.5 | 252.7 ± 87.6 |
| 0.5 ml of 2% CGF plus 0.5 ml 2% NaTPP | 1.0 | 224.4 ± 23.3 |
| 0.5 ml of 2% CGF plus 0.5 ml 10% NaTPP | 5.0 | 93.2 ± 5.8 |

The results of these experiments demonstrated the sensitivity of the gel strength to NaTPP:chitosan mass ratio of the gel composition. Further, the results of these experiments indicated that the highest gel strengths were achieved at NaTPP:chitosan mass ratios ranging from about 0.5:1 to about 1:1.

Example 2: Validation of Determination of Additional Active Agent Enzymatic Activity The following experiments were conducted to ensure accurate determinations of enzymatic activity of an additional active agent, thrombin, loaded into the gel solution.

To determine the presence of enzymatically active thrombin, a highly specific chromogenic thrombin substrate (Aldrich Cat # T3068, Sigma-Aldrich, St. Louis, Mo.) was utilized. This thrombin substrate includes a cleavably linked beta-Ala-Gly-Arg para-nitroanilide. Upon contact with enzymatically active thrombin, release of the p-nitroanilide from the peptide linkage generates a UV absorbance around 405 nm.

To ensure minimal exposure to other enzymes or biologically active materials which may cause either substrate cleavage or thrombin degradation, the solution used for dissolving all enzymes and substrates was phosphate buffered saline (PBS) (10× concentrated, Aldrich Cat # P5493, Sigma-Aldrich, St. Louis, Mo.), aseptically diluted to 1× using BPC grade water (Aldrich Cat # W3513, Sigma-Aldrich, St. Louis, Mo.). The PBS solution was 0.2 µm filtered (Nalgene Cat #190-2520, Thermo Fisher Scientific Inc., USA) prior to use to maintain sterility. The solutions were produced in a labconco purifier class II hood that had been sprayed down with 70% ethanol solution and UV light exposed for 20 minutes prior to initiating work to reduce bacterial contamination.

Thrombin from human plasma lyophilized powder (Aldrich Cat # T8885, Sigma-Aldrich, St. Louis, Mo.) was diluted in 5 ml of PBS thus forming a 3.2 U/ml thrombin solution. The thrombin substrate was also dissolved in 5 ml of PBS forming a 5 mg/ml substrate solution.

A positive control (thrombin-positive) sample was generated by combining 0.1 ml of the substrate solution along with 0.1 ml of the thrombin solution and 1.8 ml of PBS. A negative control (thrombin-negative) sample was generated by combining 0.1 ml of the substrate solution in 1.9 ml of PBS. Both samples were incubated at 37° C. overnight. The next day the positive sample was visibly observed to be yellow in color while the negative sample was still clear.

Figure 2:
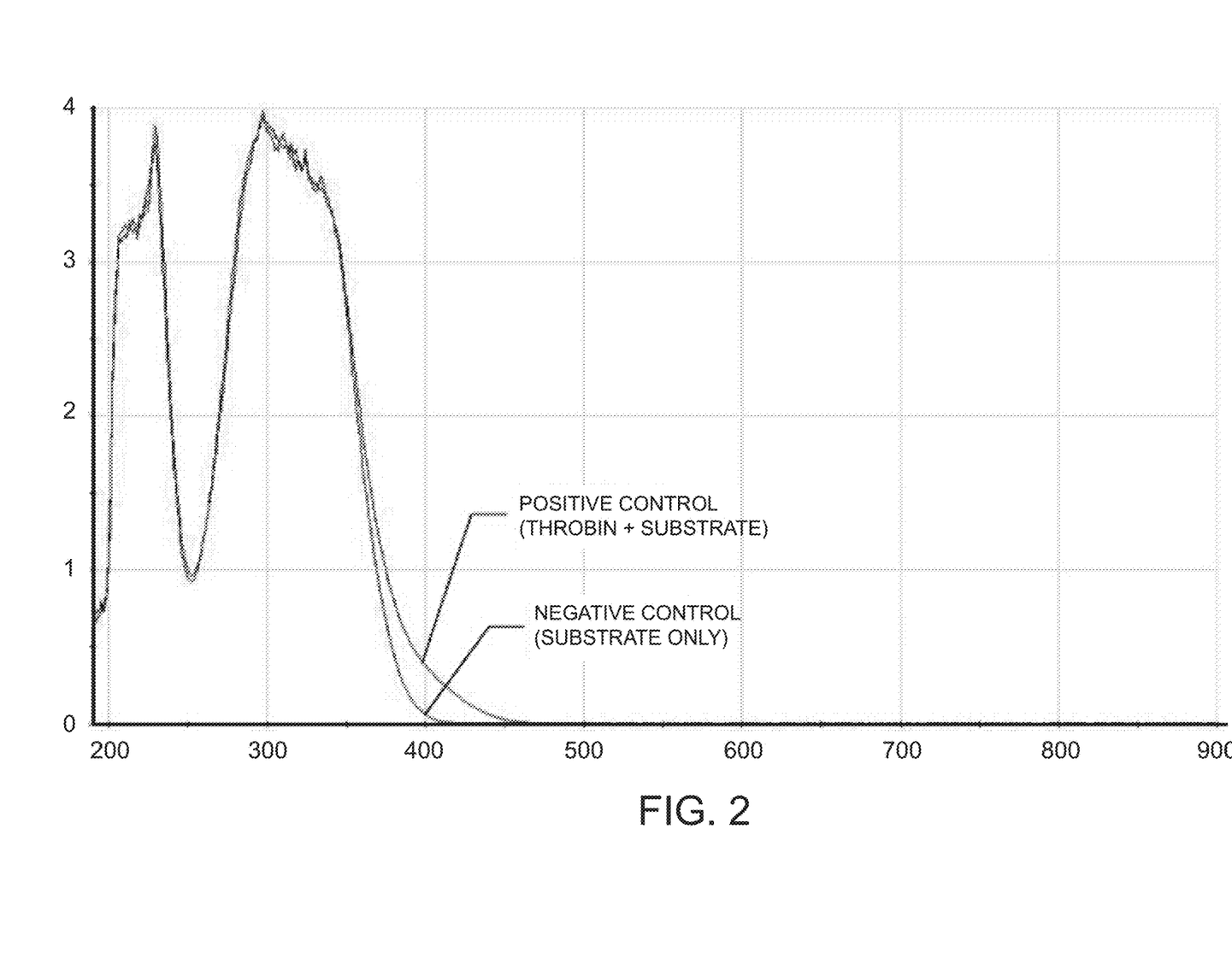
FIG. 2 is a graph summarizing absorbance spectra of a buffered positive control sample including thrombin and a substrate, and a buffered negative control sample including the substrate only, using the buffer solution alone as a blank.
Figure 3:
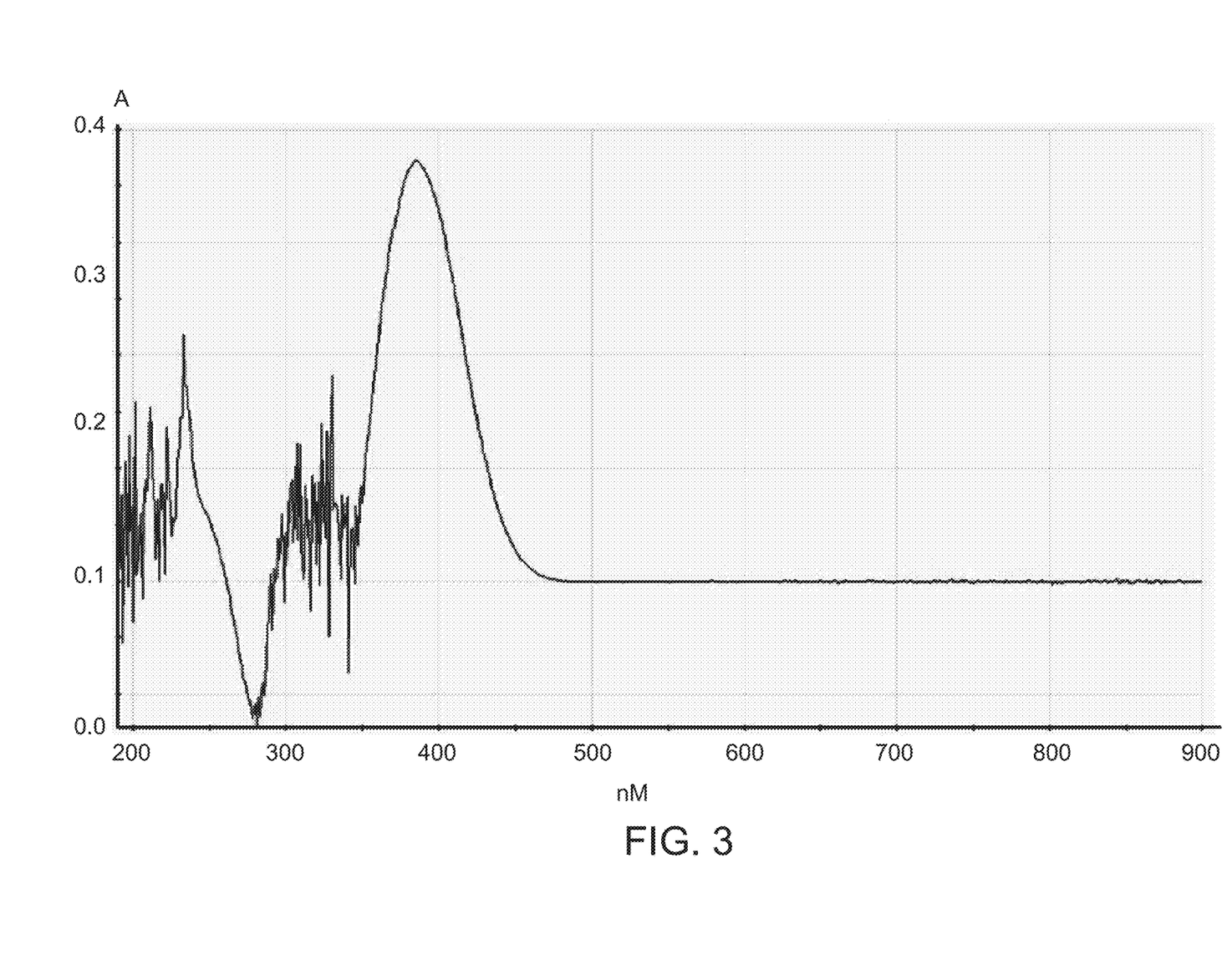
FIG. 3 is a graph summarizing absorbance spectra of the buffered positive control sample of FIG. 2 using the buffered negative control sample of FIG. 2 as a blank.

The positive control sample and the negative control sample were subjected to absorption spectroscopic analysis in the UV and visible wavelength ranges. FIG. 2 is a graph summarizing the UV/Vis absorption spectra of the positive and negative control samples scanned against a blank of 2 ml of PBS. To focus on the difference between the positive and negative control samples (i.e. the signal produced by the addition of thrombin), a UV/Vis absorption spectrum of the positive control samples was obtained using the negative control sample as the blank; the obtained spectrum is summarized in FIG. 3. Referring to FIG. 2 and FIG. 3, the peak difference in absorbance between the positive and negative control samples was observed at 385 nm.

The results of this experiment validated the assay for enzymatically active thrombin using the chromogenic thrombin substrate described above. The assay exhibited peak sensitivity at an assay wavelength of 385 nm. Based on this finding, an assay wavelength of 385 nm, as well as an assay wavelength of 405 nm suggested by the manufacturer, were selected for use in subsequent thrombin release experiments described below. Further, due to the relatively low UV absorption exhibited in the results of this experiment, the amount of thrombin substrate solution was doubled to 0.2 mL for use in subsequent thrombin release experiments.

Example 3: Preservation of Enzymatic Activity of Additional Active Agent

The following experiments were conducted to ensure that an enzyme-based additional active agent, thrombin, loaded into the gel solution retained its enzymatic activity after storage and after clotting proximate a surgical site.

A series of samples were produced for the various compositions as summarized in Table 2 below. Negative and positive control samples similar to those described in Example 2 were produced, as well as various combinations of the thrombin solution described in Example 2 with a gel solution formed from Chitosan (Aldrich Cat #419419, Sigma-Aldrich, St. Louis, Mo.) dissolved at 2% w/v in a first solvent solution of 1% v/v L-lactic acid. Referring to Table 2, samples were produced containing 2% chitosan only, and thrombin only. Additional samples were produced in which thrombin was added to the chitosan gel solution, to which mixture was added a hardener solution formed from sodium tripolyphosphate (NaTPP, Aldrich Cat #238503) dissolved in a second solvent of de-ionized water (DiH$_2$O). All samples were mixed in 2 ml plastic vials.

After mixing at 37° C. and 100 RPM for 5 minutes, 0.2 ml aliquots of the supernatant (excluding solid gel if formed) from each sample vial was pulled and mixed with 0.2 ml of the substrate solution described in Example 2, along with 1.6 ml of PBS. Additional samples in which thrombin was added to the chitosan gel solution, to which mixture the NaTPP hardener solution was added subsequently, were further incubated at 37° C. for 30 minutes and for 1 hour prior to pulling supernatant aliquots for subsequent analysis. The mixtures of supernatant aliquots and substrate solution were then incubated overnight at 37° C. and subsequently analyzed to assess the UV absorbance of each mixture at wavelengths of 385 nm and 405 nm as compared to a PBS blank in order to assess the enzymatically active thrombin content of each aliquot.

The results of the UV absorbance analysis are summarized in Table 2 below. Referring to Table 2, the sample absorbance at a wavelength of 405 nm was determined to be more discriminatory for enzymatically active thrombin content than the corresponding absorbance at a wavelength of 385 nm. The negative control sample had very low absorbance (0.071) and there was relatively low indication of interference from chitosan alone, NaTPP alone, or the mixture of chitosan and NaTPP (absorbance <0.2 for all corresponding samples) which indicates that the substrate solution is suitably selective so as to be cleaved by enzymatically active thrombin, rather than by other non-specific agents such as pH changes or ionicity. Thrombin activity was observed in the sample of thrombin mixed with PBS but, interestingly, the measured thrombin activity was relatively low as compared to the thrombin-loaded chitosan gel solution samples. No significant difference in thrombin activity was observed between the samples in which thrombin was mixed first with the chitosan gel solution and the sample in which thrombin was mixed first with the NaTPP hardener solution, indicating that neither solution denatures the thrombin enzyme. Incubating the resulting thrombin-loaded solid hydrogel at 37° C. for longer periods of time did not decrease enzymatic activity, and indeed appeared to enhance enzymatic activity slightly. It should be noted that the results described below are relative measures of enzymatic activity among samples, rather than exact quantifications of absolute enzymatic activity levels.

TABLE 2

UV/Vis Absorbance of Thrombin Released from Hemostatic Gel Compositions.

| Sample Description | Absorbance (385 nm) | Absorbance (405 nm) |
|---|---|---|
| Negative control (0.2 ml of substrate and 1.8 ml of PBS) | 0.603 | 0.071 |
| Positive control (0.2 ml of substrate, 0.2 ml of thrombin and 1.6 ml of PBS) | 2.269 | 1.404 |
| Sample 0.5 ml 2% NaTPP + 0.5 ml PBS | 0.666 | 0.106 |
| Sample 0.5 ml 2% Chitosan + 0.5 ml PBS | 0.650 | 0.072 |
| Sample 0.5 ml 2% NaTPP + 0.5 ml 2% Chitosan | 0.677 | 0.114 |
| Sample 0.2 ml Thrombin + 1 ml PBS | 0.913 | 0.314 |
| Sample 0.2 ml Thrombin + 0.5 ml 2% Chitosan (mixed first), then added 0.5 ml 2% NaTPP | 1.446 | 0.737 |
| Sample 0.2 ml Thrombin + 0.5 ml 2% NaTPP (mixed first), then added 0.5 ml 2% Chitosan | 1.513 | 0.797 |
| Sample 0.2 ml Thrombin + 0.5 ml 2% Chitosan (mixed first), then added 0.5 ml 2% NaTPP gel incubated 37° C./100 RPM for 30 min prior to sampling | 1.813 | 1.036 |
| Sample 0.2 ml Thrombin + 0.5 ml 2% Chitosan (mixed first), then added 0.5 ml 2% NaTPP gel incubated 37° C./100 RPM for 1 hour prior to sampling | 1.800 | 1.024 |

The results of the experiment demonstrated that a solid formed from the flowable hemostatic gel composition including an enzyme-based additional active agent described herein released the chitosan in an enzymatically active form. Further, the release of the enzymatically active agent was relatively insensitive to various factors in the production of the flowable hemostatic gel composition, including order of mixing ingredients and incubation time used to form the gel.

Example 4: Verification of Stable Storage and Differential Loading Ability of Enzyme-Based Additional Active Agent The following experiments were conducted to verify stable storage of the flowable hemostatic gel composition with an added enzyme-based additional active agent, and to validate an ability to tailor the loading of the enzyme-based additional active agent for therapeutic effect.

A series of mixtures were formed from 2% w/v chitosan gel solution, as described in Example 1, combined with varying volumes of 3.2 U/ml thrombin solution, as described in Example 2, with gentle shaking at room temperature overnight to fully incorporate the thrombin into the chitosan gel solution. For comparison, the mixture of 0.2 ml thrombin and 0.5 ml of 2% w/v chitosan solution formed previously in Example 3 also was obtained for use in these experiments to further assess the effect of storage time on thrombin activity. The thrombin content of each solution is summarized in Table 3 below.

TABLE 3

Chitosan-Thrombin Mixtures Used in Gel Compositions.

| Thrombin Content (% v/v) | Mixture Method (note thrombin solution is 3.2 U/ml) | Theoretical Units Thrombin/Gram Chitosan (U/g) |
|---|---|---|
| 1% | 0.01 ml thrombin + 0.99 ml 2% chitosan | 2 |
| 5% | 0.05 ml thrombin + 0.95 ml 2% chitosan | 8 |
| 10% | 0.1 ml thrombin + 0.9 ml 2% chitosan | 18 |
| 25% | 0.25 ml thrombin + 0.75 ml 2% chitosan | 53 |
| 50% | 0.5 ml thrombin + 0.5 ml 2% chitosan | 160 |
| 0.2 ml Thrombin + 0.5 ml 2% Chitosan (earlier test, included for reference) | See Example 2 | 64 |

After mixing overnight, each thrombin/chitosan solution was split into two 0.5 ml aliquots. The first aliquot from each solution was put in the bottom of a vial and 0.5 ml of 2% NaTPP hardener solution was added on top to form "chitosan first" compositions. The second aliquot from each solution was pipetted into a vial which already contained 0.5 ml of 2% NaTPP hardener solution to form "NaTPP first" compositions. These compositions were incubated at 37° C./100 RPM for 2 hours, and then 0.2 ml of supernatant was pulled from each sample and tested for thrombin activity as described in Example 3. The samples tested for thrombin activity are summarized in Table 4 below.

TABLE 4

Thrombin Release from Thrombin Loaded Gel Compositions

| Sample Description | Absorbance at 385 nm | Absorbance at 405 nm |
|---|---|---|
| Negative control (0.2 ml of substrate and 1.8 ml of PBS) | 0.624 | 0.073 |
| Positive control (0.2 ml of substrate, 0.2 ml of thrombin and 1.6 ml of PBS) | 2.261 | 1.394 |
| Chitosan plus thrombin (2 U/g) chitosan first | 0.663 | 0.095 |
| Chitosan plus thrombin (8 U/g) chitosan first | 0.669 | 0.1 |
| Chitosan plus thrombin (18 U/g) chitosan first | 0.695 | 0.111 |
| Chitosan plus thrombin (53 U/g) chitosan first | 0.955 | 0.332 |
| Chitosan plus thrombin (160 U/g) chitosan first | 1.592 | 0.85 |
| Chitosan plus thrombin (2 U/g) NaTPP first | 0.637 | 0.084 |
| Chitosan plus thrombin (8 U/g) NaTPP first | 0.685 | 0.111 |
| Chitosan plus thrombin (18 U/g) NaTPP first | 0.706 | 0.128 |
| Chitosan plus thrombin (53 U/g) NaTPP first | 0.824 | 0.224 |
| Chitosan plus thrombin (160 U/g) NaTPP first | 1.029 | 0.381 |

Figure 4:
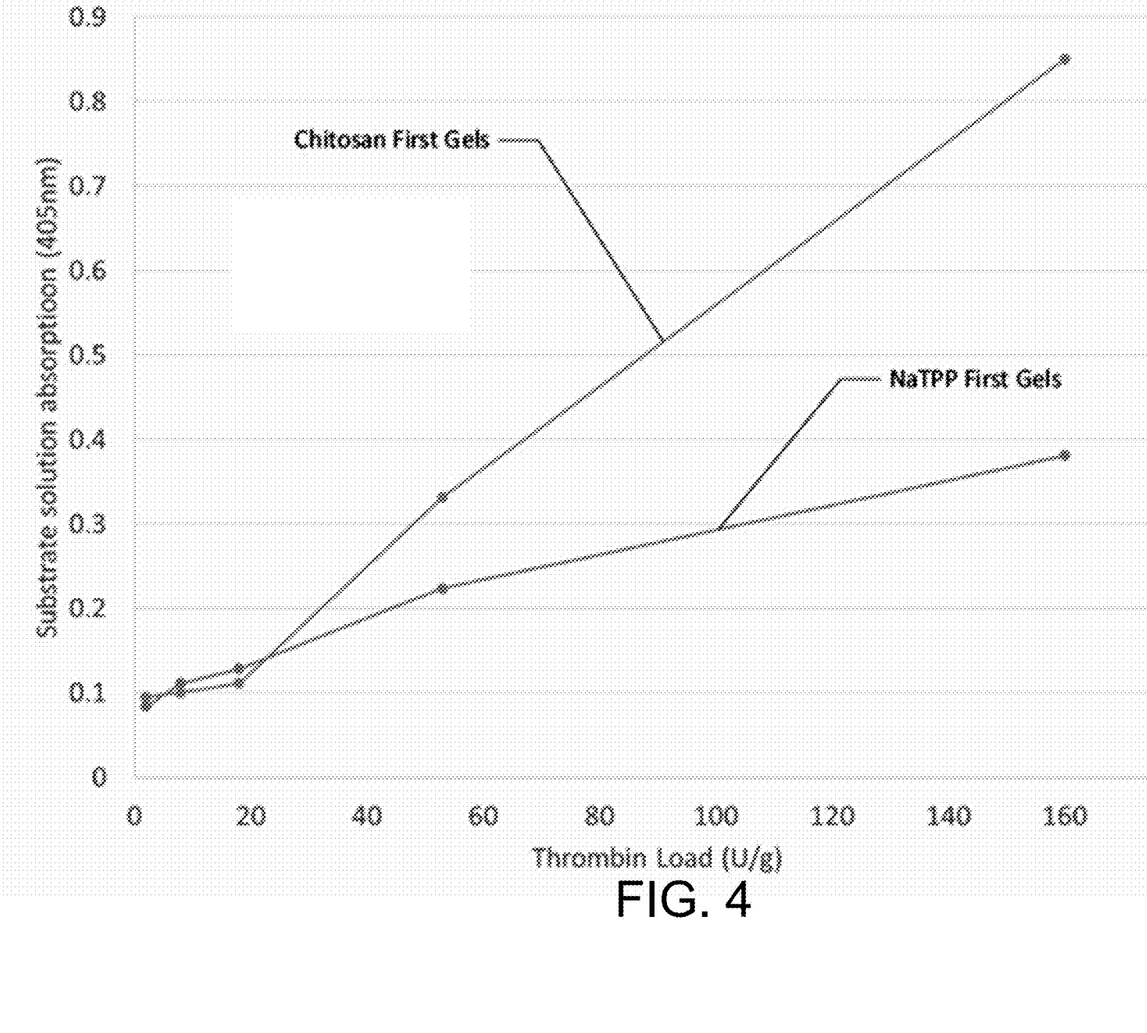
FIG. 4 is a graph summarizing a release of enzymatically active thrombin from a hemostatic gel composition as a function of thrombin loading of the hemostatic gel composition.

FIG. 4 summarizes the relative changes in thrombin activity, measured as absorbance at 405 nm, as a function of thrombin loading for the gel compositions tested. These relative curves for the chitosan-first compositions and the NaTPP-first compositions generally indicate a dose-dependent relationship with respect to thrombin loading of the gel solution, in which higher quantities of thrombin cleave more of the substrate used to assay thrombin activity. Note that the thrombin content of the test solutions analyzed in this experiment ranged from 0.0032 U to 0.32 U, whereas the thrombin content of the positive control from Ex. 3 contained 0.64 U.

The results of this experiment demonstrate a dose-dependent relationship of release of the additional active agent from the resulting solid with respect to the amount of additional active agent loaded into the flowable hemostatic gel composition.

Example 5: Effect of Composition of Gel Compositions on Gelling Properties

The following experiments were conducted for various two-part gel compositions to assess gelation speed, occlusion, and gel strength for application as a hemostatic gel.

The two part mixture gels included ionic gels formed by combining 2% NaTPP with a polycationic polymer, in this case 2% chitosan, a polysaccharide as described above. In some cases, the two-part mixture gels further included polyelectrolyte complexes (PEC) formed by combining 2% w/v chitosan in acid solution and 2% sodium alginate in alkaline solution. The sodium alginate is another polysaccharide, and an anionic copolymer, such that the combination of the chitosan and alginate solutions yielded a near pH neutral solution and the alginate and chitosan were attracted to each other by their respective ionic interactions. For all solutions other than chitosan, the material was dissolved in water. For chitosan, the solution was done in either 0.1M HCl or 1% v/v acetic acid. The following polysaccharides were obtained from Aldrich: Chitosan medium molecular weight ("MMW")-75-85% deacetylation, viscosity 200-800 cP, 1 wt. % in 1% acetic acid (25° C., Brookfield); Chitosan low molecular weight ("LMW")→75% deacetylation, viscosity 20-300 cP, 1 wt. % in 1% acetic acid (25° C., Brookfield); and Sodium Alginate—Brookfield viscosity 100-300 cP, 2% (25° C.). Note that the polysaccharide is referred to below as the "gel" and the polyvalent counterion (NaTPP) is referred to as the "hardener."

Two-part mixture tests were attempted on a rheometer, however they were unsuccessful as gelation was so fast as to prevent proper loading. The kinetics of these tests were video recorded instead as detailed below. Video recording (described below) was used to assess the gel kinetics of the two-part get mixtures due to the short time scale of gelling relative to the measurement speed capabilities of the rheostat.

The solidified gel was subjected to an occlusion test in order to determine its capability to retain fluids. For this test, the gel was set up by mixing 1 ml each of gel and hardener in the bottom of a 12 ml syringe with a standard Leur tip and a Leur cap. For each test, the gel was set up in the syringe either by mixing or by heating to 37° C. followed by addition of water and removal of cap. Table 5 summarizes the result properties observed using videotaped gelling of each mixture.

TABLE 5

Occlusion testing results.

| Gel | Observation |
|---|---|
| 2% Sodium alginate + 2% CaCl2 | Held water for over 3 days, discarded while still full |
| 2% Sodium alginate/0.1M NaOH + 2% MMW chitosan 0.1M HCl | Instant failure, all water pass through |
| 2% Sodium alginate/0.1M NaOH + 2% LMW chitosan 0.1M HCl | Held water initially, all leaked out after 3 days |
| 2% MMW chitosan 0.1M HCl + 2% NaTPP | Held, 3 ml passed through and then occluded successfully for over nine days |
| 2% LMW chitosan 0.1M HCl + 2% NaTPP | Instant failure, all water pass through |

Note that occlusion was not just a test of gel strength but capacity to stop flow, which relates to overall gel properties. In these experiments, occlusion was assessed as the ability to prevent flow through an orifice of approximately 2 mm diameter.

Mechanical test: Testing was performed on a TA.XTplus analyzer for the two-part mixtures as follows. Into a two-mL microfuge tube, 0.5 ml of gelling agent and 0.5 ml of hardener were added by pipette and allowed to mix and equilibrate for 30 minutes in a 100 RPM/37° C. shaking incubator. Subsequently a 0.25 inch steel ball was forced into the set gel at a crosshead speed of 1 mm/sec to a depth of 3.2 mm (up to the ball midpoint) with testing initiated at 2 g of resistance force. The maximum resistance force encountered during the test was recorded to determine relative gel strength as summarized in Table 6.

TABLE 6

Mechanical testing results.

| Composition | Max Force (g) |
|---|---|
| alginate 2% in with 0.5 ml 2% calcium chloride stirred together (unequilibriated) | 4.125 |
| 2% chitosan MMW (2%/1% HOAc) with 2% NaTPP (unequilibriated) | 7.938 |
| 2% chitosan (LMW/0.1M HCl) with 2% NaTPP | 17.793 |
| 2% chitosan (LMW/0.1M HCl) with 2% alginate (0.1M NaOH) | 173.206 |
| 2% chitosan (MMW/1% HOAc) with 2% NaTPP | 14.327 |
| 2% chitosan (MMW/1% HOAc) with 2% alginate in 0.1M NaOH | 13.31 |
| 2% chitosan (MMW/1% HOAc) with 2% alginate in 0.01M NaOH | — |
| 2% chitosan (MMW/0.1M HCl) with 2% alginate in 0.1M NaOH | 151.1 ± 83.2 (STDEV, N = 6) |
| 2% chitosan (MMW/0.1M HCl) with 2% alginate in 0.01M NaOH | 3.847 |
| 2% alginate with 2% calcium chloride | 32.374 |

Referring to Table 6, the highest mechanical strength was observed with polyelectrolyte complexes between chitosan and alginate when the chitosan was in 0.1M HCl and alginate in 0.1M NaOH. Suitable strength was observed for both low and medium MW chitosan mixtures as well as alginate plus calcium chloride which exhibited slightly lower gel strength.

Video Speed Testing: Due to the speed at which the two part mixes set up relative to the sampling rate associated with rheological detection, the set-up rate of the two-part mixes was qualitatively recorded by video recording a mixture of the two materials. An injection system was generated by combining two 1-ml syringes with rubber tubing and a Y-shaped adaptor for simultaneous injection. Video records were obtained of each mixed system during injection, with red dye added to enhance visualization, as summarized in Table 7. For the purposes of visualization, red dye was added.

TABLE 7

Video Speed Testing Results

| Mixture | Description and Notes |
|---|---|
| 2% calcium chloride with 2% sodium alginate (red dyed alginate). | Solid red alginate gel formed instantly. |
| 2% NaTPP in water (clear) with 2% chitosan LMW in 1% acetic acid (red dyed chitosan). | Gelled chitosan formed instantly. |
| 2% chitosan MMW in 0.1M HCl with 2% sodium alginate in 0.1M NaOH. (red dyed alginate). | Chitosan gelled instantly upon mixing but red dye remained liquid, indicating much of alginate solution was not gelled. |

Referring to Table 7, the gelation of each of these mixtures is extremely rapid and in each case occurred in less than 1 second.

The results of these experiments revealed several advantageous aspects. Regarding speed of gelling, each of the two-part mixtures gelled essentially instantly and formed strong gels, with the strongest being obtained with polyelectrolyte complexes including both alginate and chitosan. Regarding occlusion, mixtures of chitosan with NaTPP and of alginate with calcium chloride were effective at preventing leakage, although polyelectrolyte mixtures including both alginate and chitosan were less effective over extended periods. In addition, the chitosan/NaTPP and polyelectrolyte gels are very biocompatible as each of NaTPP, calcium chloride, chitosan, and alginate is assigned status "generally regarded as safe" (GRAS) by the FDA for food usage, indicating low toxicity for these compounds. Chitosan is also known to induce blood clotting as an advantage.

Example 6: Effect of Ingredient Proportions of Gel Properties

The following experiments were conducted to assess the effects of different proportions of ingredients for various two-part mixtures of gels in terms of gelation speed, occlusion, and gel strength for applications as a hemostatic gel.

The gels used were NaTPP with chitosan compositions. A series of chitosans were utilized, including: Chitosan medium molecular weight ("MMW")—75-85% deacetylation, viscosity 200-800 cP, 1 wt. % in 1% acetic acid (25° C., Brookfield) (Aldrich Cat #448877); Chitosan low molecular weight ("LMW")→75% deacetylation, viscosity 20-300 cP, 1 wt. % in 1% acetic acid (25° C., Brookfield) (Aldrich Cat #448869); Chitosan shrimp shells practical grade ("CPG") (>200 cP, 1 wt. % in 1% acetic acid (20° C., Brookfield) (lit.)≥75% deacetylated) (Aldrich Cat #417963); Chitosan from shrimp shells ("CSC"), ≥75% (deacetylated) bulk density 0.15-0.3 g/cm3) (Aldrich Cat # C3646); and Chitosan Coarse ground flakes and powder ("CGF"), >75% deacetylation, 800-2000 cP, 1 wt. % in 1% acetic acid (25°

C., Brookfield) (lit.) (Aldrich Cat #419419). For the two-part mixtures, the polysaccharide (chitosan) is referred to below as the "gel" and the polyvalent counterion (NaTPPP) is referred to as the "hardener."

The solidified gels were mechanically tested by the method described in Example 5. Table 8 below summarizes results of this testing. For these tests, the chitosan solutions were dissolved in 1% (v/v) L-lactic acid, because lactic acid is non-volatile (longer shelf-life), is a natural metabolic product found inside the human body (increased biocompatibility), and has an established USP monograph. The primary testing was performed using 2% w/v chitosan, but additional solutions containing chitosan types CGF and MMW were formed at 3% w/v and 4% w/v concentrations in 1% L-lactic acid. The CGF dissolved at 3% w/v in 1% L-lactic acid but the other chitosan mixtures only partially dissolved. Also, mixtures using pH alkaline buffers for the NaTPP solution were formed using pH buffers of (i) 1% w/v sodium citrate (pH 7.93), and (ii) 0.01M $Na_2CO_3$ (pH 10.32). The use of these buffers had no effect on gel strength.

TABLE 8

Mechanical testing results.

| Description | Max Force (g) ± STDEV (N = 3) |
|---|---|
| 0.5 ml of 2% MMW plus 0.5 ml 2% NaTPP | 85 ± 34 |
| 0.5 ml of 2% CPG plus 0.5 ml 2% NaTPP | 10 ± 3 |
| 0.5 ml of 2% CSC plus 0.5 ml 2% NaTPP | 11 ± 6 |
| 0.5 ml of 2% LMW plus 0.5 ml 2% NaTPP | 12 ± 8 |
| 0.5 ml of 2% CGF plus 0.5 ml 2% NaTPP | 84 ± 75 |
| 0.5 ml of 2% LMW plus 0.5 ml 2% NaTPP in 0.01M $Na_2CO_3$ | 5 ± 2 |
| 0.5 ml of 2% LMW plus 0.5 ml 2% NaTPP in 1% w/v sodium citrate | 11 ± 10 |
| 0.5 ml 3% CGF chitosan plus 0.75 ml of 2% NaTPP | 272 ± 46 |
| 0.5 ml 3% CGF chitosan plus 0.15 ml of 10% NaTPP | 20 ± 12 |

NOTE:
Chitosan in 1% L-lactic acid and NaTPP in deionized water unless otherwise specified The results of these experiments indicate that the gel compositions containing medium molecular weight chitosan and coarse ground flake chitosan generated the strongest gels. The highest gel strength was achieved using a 3% w/v solution of CGF mixed with 0.75 ml of 2% NaTPP; a higher volume of NaTPP was utilized to ensure the mass of chitosan was same as the mass of NaTPP. Compositions containing equivalent mass of CGF and higher concentrations of NaTPP did not result in improved gel proportions, possibly due to the need for the ions to be dilute enough to move about to properly crosslink the chitosan chains. Further variations in NaTPP/chitosan ratio may result in improved gel-strength and occlusion properties.

Example 7: Adhesion Properties of Bioadhesive Compositions

The following experiment was conducted to assess the adhesion properties of chitosan/NaTPP gels to be used as a bioadhesive.

In order to assay bio-adhesion, a bioadhesion probe fixture assay was developed for the TA.XTplus. A commercial gel mucoadhesion probe (Texture Technologies part number: A/GMP) was purchased and mounted onto a custom built bracket constructed of 0.5 inch thick acrylic mounted onto the current TA-90 stage by #10-24 bolts and thumbscrews. Traditional mucoadhesion testing was performed using pork loin to represent typical human muscle tissue.

Bioadhesion was tested using the TA.XTplus instrument by dropping the probe down onto the adhesion surface at 0.5 mm/sec, applying 500 grams of force for 10 seconds, and then retracting the probe at 0.5 mm/sec while measuring the downward pulling reaction force on the probe upon retraction due to adhesion. The mucoadhesion probe was prepared by adding 0.5 ml of 2% chitosan in 0.1M acetic acid and 0.5 ml of 2% NaTPP sequentially into a plastic collar surrounding the probe to create the formulated chitosan-NaTPP gel. After setting for 1.5 hours, this gel was inverted and run through adhesion testing against the prepared sample of pork loin wetted with phosphate buffered saline (pH 7.4). A positive force peak upon probe retraction due to the adhesion was recorded, as summarized in Table 14. A series of samples including chitosan-NaTPP combined with poly (acrylamide-co-acrylic acid), poly(acrylic acid), and poly (vinylpyrrolidinone) were also tested.

TABLE 14

Chitosan Formulation and Results for Adhesion test

| Formulation | Max adhesion force (N) |
|---|---|
| Chitosan-TPP | 1.094 |
| Chitosan-TPP + poly(acrylamide-co-acrylic acid) | 0.845 |
| Chitosan-TPP + poly(acrylic acid) | 0.778 |
| Chitosan-TPP + poly(vinylpyrrolidinone) | NA |
| Steel to pork (no gel) | 1.161 |

Referring to Table 14, under these testing conditions, all gels exhibited lower adhesion compared to the adhesion of the bare probe against the wetted pork. However, the adhesion loss typically occurred between the steel probe and the gel, rather than between the pork and the gel. For example, the poly(vinylpyrrolidinone) sample delaminated cleanly from the steel tip. Because the goal is for a surgical glue to connect tissue to tissue, rather than tissue to stainless steel, adhesion loss between the steel probe and the gel is not deemed to indicate unsuitability of adhesion. Instead, modified testing methods were employed as described in the following examples.

Example 8: Adhesional Longevity of Chitosan Bioadhesive Gels

The following experiment was conducted to assess formulated chitosan materials used to produce bioadhesive.

Phosphate buffered saline (PBS) was generated by dissolution of Aldrich tablets per manufacturer directions, as described above. Additionally, sodium azide was added to the solution to yield a final concentration of 0.1% sodium azide (w/v) in the PBS, to prevent microbial growth. Freshly purchased and refrigerator-stored pork-loin was cut into squares approximately 1.5 inch in distance along the sides. A series of 10-oz plastic dishes was prepared by affixing a single thumbtack using two-part epoxy to the bottom middle of the dish, point side up, and by cleaning with 70% ethanol. For each test, the pork piece was pushed down onto the thumbtack point to affix the pork piece to the plate. A one-inch long stir bar was placed in each dish to provide agitation during testing. The dishes were placed on a Fisher Isotemp stirring hotplate with magnetic stirring at 100 RPM and gentle surface warming at 40° C. from the bottom of the plates. A Logitech Pro 9000 webcam was placed directly overhead in order to record movies and images from two dishes, which were tested at the same time. For each sample, 0.5 ml of the mixed gel solution as summarized in Table 15 was pipetted onto the middle of the pork piece and then 0.5 ml of 2% (w/v) NaTPP was added. The solution was allowed to set for approximately 2 minutes, and then PBS+azide was gently added to each dish so that it reached a 6-oz marking on the side of the dish, resulting in approximately 0.5 inch coverage over the pork surface. As the dish was stirred and heated, image recording by the webcam observed how long the bioadhesive samples retained their gel adhesion. A small quantity of methylene blue dye was added to each sample to aid contrast and to facilitate observations in the photo series.

TABLE 15

Samples used in gel longevity test.

|   | Methylene blue (2 mg/ml) | Chitosan in Solution (2% w/v) | Solvent | Bioadhesive Agent |
|---|---|---|---|---|
| 1 | 50 µl | 1 ml CGF | 0.1M HOAc | — |
| 2 | 50 µl | 1 ml MMW | 1% L-lactic acid | — |
| 3 | 50 µl | 0.75 ml MMW | 1% L-lactic acid | 0.25 ml of 1.8 kDa poly(acrylic acid) |
| 4 | 50 µl | 0.75 MMW | 1% L-lactic acid | 0.25 ml 1.3 MDa poly(vinyl-pyrrolidinone) |
| 5 | 50 µl | 0.5 ml MMW | 1% L-lactic acid | 0.5 ml of 1.8 kDa poly(acrylic acid) |
| 6 | 50 µl | 0.25 ml MMW | 1% L-lactic acid | 0.75 ml of 1.8 kDa poly(acrylic acid) |

The results of these experiments indicated that of the tested gels, two of the samples, (3) 50 µl of 2 mg/ml methylene blue, 0.75 ml chitosan MMW (Aldrich #448877) 2% w/v in 1% L-lactic acid, 0.25 ml poly(acrylic acid) (MW 1800 Da) and (5) 50 µl of 2 mg/ml methylene blue, 0.5 ml chitosan MMW (Aldrich #448877) 2% w/v in 1% L-lactic acid, 0.5 ml poly(acrylic acid) (MW 1800 Da), were observed to have the best adhesional longevity, with strong adhesion visible even after 12 hours. Furthermore, it is worth noting that the poly(acrylic acid) mixed with chitosan separately formed into a viscous, partially gelled mixture even prior to combining with the NaTPP. This interaction is likely due to hydrogen bonding between poly(acrylic acid) and chitosan. This property may be beneficial for usage as a bioadhesive, as a partially gelled substance tends to remain at the location where it is applied.

Example 9: Adhesional Strength of Chitosan Bioadhesive Gels

The following experiment was conducted to assess the adhesional longevity of formulated chitosan materials used to form bioadhesives.

As a stimulant for human tissue, freshly obtained pork-loin with minimal processing was again used. This test was performed in a similar manner as detailed in Example 8 with modifications as described below to assess pork-to-pork (i.e., tissue-to-tissue) adhesion. A first piece of pork was cut into a 2 cm×2 cm square, and a second piece of pork was cut into a 4 cm×4 cm square. The larger piece was sandwiched between two plastic pieces with a hole cut through the top piece, then mounted onto the platform of the TA instrument. A hook with a screw end was placed in the smaller piece and clamped on the top tensile grip of the TA instrument to form a pork adhesion probe. A volume of 0.5 mL of PBS with 0.1% sodium azide was added to the pork to moisten it, and a solution to be tested was then applied to the pork. The pork adhesion probe was lowered until the top pork piece met the pork mounted to the TA instrument platform, and approximately a 1 N compressive force was held on the pork adhesion probe for 10 seconds. Afterwards, the pork adhesion probe was retracted at a speed of 0.5 mm/sec, while measuring the downward pulling force on the probe upon retraction due to pork-to-pork adhesion.

The sample solutions tested, and corresponding maximum adhesion force (N) values, are summarized in Table 16. The chitosan solution used for these tests was MMW chitosan 2% w/v in 1% v/v L-lactic acid solution. The poly(acrylic acid) solution used was poly(acrylic acid) (MW 1800 Da, Aldrich Cat #323667) 25% w/v in distilled water.

TABLE 16

Sample Solution and Force (N) for Adhesion Test

| Sample | Sample Solution | Force (N) |
|---|---|---|
| Control | None | 0.084 |
| A | 25:75 premix of polyacrylic Acid:Chitosan solution | 0.286 |
| B | 12.5:37.5:50 (premix of 25:75 polyacrylic Acid:Chitosan solution):NaTPP solution | 0.376 |
| C | 50:50 premix of polyacrylic acid:Chitosan solution | 0.141 |
| D | 25:25:50 (premix of 50:50 polyacrylic acid:Chitosan solution):NaTPP solution | 0.166 |

Referring to Table 16, the strongest force measured was obtained from a 25:75 v:v mixture ratio of 25% poly(acrylic acid) mixed with 2% chitosan solution and set with NaTPP, likely resulting from the strong hydrogen bonding obtained from poly(acrylic acid).

Exemplary embodiments of a hemostatic gel composition and methods of use are described above in detail. The methods and compositions are not limited to the specific embodiments described herein, but rather, operations of the methods and components of the systems may be utilized independently and separately from other operations and/or components described herein. For example, the methods and compositions described herein may have other industrial and/or consumer applications and are not limited to practice in medical applications as described herein. Rather, one or more embodiments may be implemented and utilized in connection with other industries.

As used herein, an element or step recited in the singular and proceeded with the word "a" or "an" should be understood as not excluding plural said elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of inhibiting bleeding from a site of a defect within a biological tissue, said method comprising:
   applying a flowable gel solution to the site, the flowable gel solution including:
   a solvent comprising water and an acid at about 0.075 percent to about 3.75 percent (v/v) of the water;
   a polycationic hemostatic biopolymer dissolved in the solvent;
   a bioadhesive additive comprising a poly(acrylic acid) dissolved in the solvent; and
   at least one clotting agent dissolved in the solvent; and
   flowing into contact with the flowable gel solution a flowable hardener solution that includes a cross-linking agent dissolved in a second solvent, such that the cross-linking agent cross-links the hemostatic biopolymer.

2. The method of claim 1, wherein said applying the flowable gel solution comprises flowing the flowable gel solution out of a lumen of an injection device.

3. The method of claim 1, wherein the hemostatic biopolymer includes chitosan and the acid comprises lactic acid.

4. The method of claim 1, wherein the at least one clotting agent is at least one of thrombin and fibrinogen.

5. The method of claim 4, wherein the hemostatic biopolymer includes chitosan and the at least one clotting agent includes thrombin, such that a mass ratio of thrombin to chitosan (U:grams of chitosan) dissolved in the solvent is in a range from about 0.5:1 to about 200:1, each U corresponding to about 0.324 µg of enzymatically active thrombin.

6. The method of claim 1, wherein the poly(acrylic acid) has a molecular weight of about 1800 Da.

7. The method of claim 1, wherein the flowable hardener solution comprises sodium tripolyphosphate dissolved in water.

8. The method of claim 7, wherein the flowable hardener solution comprises about 2% w/v of sodium tripolyphosphate dissolved in water.

9. The method of claim 1, further comprising flowing the flowable hardener solution at a volume ratio of about 1:1 to the flowable gel solution.

10. The method of claim 1, wherein an amount of the poly(acrylic acid) is about 2.5 to about 10 percent (w/v) of the solvent.

11. A method of inhibiting bleeding from a site of a defect within a biological tissue, said method comprising applying a flowable gel solution to the site, the flowable gel solution including:
    a solvent comprising water and an acid at about 0.075 percent to about 3.75 percent (v/v) of the water;
    a polycationic hemostatic biopolymer dissolved in the solvent;
    a bioadhesive additive dissolved in the solvent, the bioadhesive additive comprising a poly(acrylic acid) having a molecular weight of about 1800 Da; and
    at least one clotting agent dissolved in the solvent.

12. The method of claim 11, wherein said applying the flowable gel solution comprises flowing the flowable gel solution out of a lumen of an injection device.

13. The method of claim 11, wherein the hemostatic biopolymer includes chitosan and the acid comprises lactic acid.

14. The method of claim 11, wherein the at least one clotting agent is at least one of thrombin and fibrinogen.

15. The method of claim 14, wherein the hemostatic biopolymer includes chitosan and the at least one clotting agent includes thrombin, such that a mass ratio of thrombin to chitosan (U:grams of chitosan) dissolved in the solvent is in a range from about 0.5:1 to about 200:1, each U corresponding to about 0.324 µg of enzymatically active thrombin.

16. The method of claim 11, further comprising:
    flowing into contact with the flowable gel solution a flowable hardener solution that includes a cross-linking agent dissolved in a second solvent, such that the cross-linking agent cross-links the hemostatic biopolymer.

17. The method of claim 16, wherein the flowable hardener solution comprises sodium tripolyphosphate dissolved in water.

* * * * *

UNITED STATES PATENT AND TRADEMARK OFFICE
CERTIFICATE OF CORRECTION

PATENT NO. : 10,660,945 B2
APPLICATION NO. : 15/195087
DATED : May 26, 2020
INVENTOR(S) : Phillips et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 499 days.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*